Figure 1:
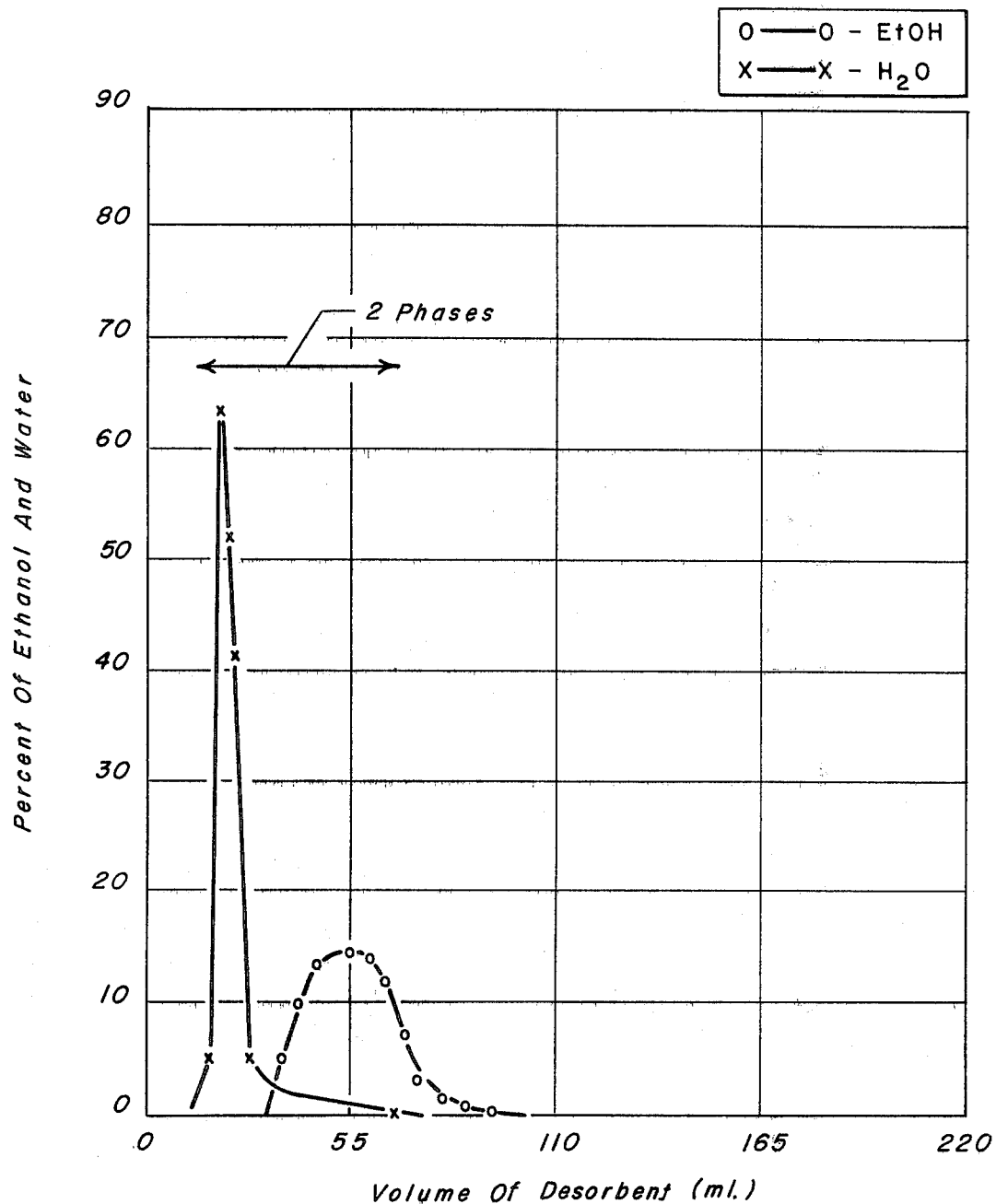

United States Patent [19]

Kulprathipanja et al.

[11] 4,382,001
[45] May 3, 1983

[54] USE OF ACTIVATED CARBON FOR SEPARATION OF ETHANOL FROM WATER

[75] Inventors: Santi Kulprathipanja, Hoffman Estates; Richard W. Neuzil, Downers Grove, both of Ill.

[73] Assignee: UOP Inc., Des Plaines, Ill.

[21] Appl. No.: 316,363

[22] Filed: Oct. 29, 1981

Related U.S. Application Data

[63] Continuation-in-part of Ser. No. 202,048, Oct. 30, 1980, abandoned.

[51] Int. Cl.³ .............................................. B01D 15/02
[52] U.S. Cl. ..................................... 210/674; 210/676; 210/694; 585/820; 585/824; 585/826; 208/310 R; 252/414; 435/161; 44/56
[58] Field of Search ............... 210/674, 663, 676, 694; 585/820, 824, 826; 208/310 R; 252/414, 420; 435/161; 44/56

[56] References Cited

U.S. PATENT DOCUMENTS

| | | | |
|---|---|---|---|
| 1,614,615 | 1/1927 | Jannek | 585/824 |
| 1,866,417 | 7/1932 | Mackert | 210/694 |
| 2,254,745 | 9/1941 | Jannek | 210/694 |
| 2,474,170 | 6/1949 | Sulzbacher | 260/593 |
| 2,985,589 | 5/1961 | Broughton et al. | 210/34 |
| 3,114,782 | 12/1968 | Fleck et al. | 260/674 |
| 3,201,491 | 8/1965 | Stine et al. | 260/676 |
| 3,236,740 | 2/1966 | Smith | 435/161 |
| 3,265,750 | 8/1966 | Peck et al. | 260/666 |
| 3,485,879 | 12/1969 | Mameniskis | 585/824 |
| 3,510,423 | 5/1970 | Neuzil et al. | 208/310 |
| 3,558,732 | 1/1971 | Neuzil | 260/674 |
| 3,668,267 | 6/1972 | Hedge | 260/674 SA |
| 3,686,342 | 8/1972 | Neuzil | 260/674 SA |
| 3,997,620 | 12/1976 | Neuzil | 260/674 SA |
| 4,093,516 | 6/1978 | Lang | 435/161 |

FOREIGN PATENT DOCUMENTS 663719  5/1979  U.S.S.R. .............................. 210/694

OTHER PUBLICATIONS

Hawley, The Condensed Chemical Dictionary, Eighth Edition, 1971, New York, 877.

*Primary Examiner*—Ernest G. Therkorn
*Attorney, Agent, or Firm*—James R. Hoatson, Jr.; Louis A. Morris; William H. Page, II

[57] ABSTRACT

An adsorptive separation process for separating ethanol from a feed mixture comprising ethanol and water, which process comprises contacting the feed mixture with an adsorbent comprising activated carbon, selectively adsorbing substantially all of the ethanol to be separated to the substantial exclusion of the water and thereafter recovering high purity ethanol. A desorption step is used to desorb the adsorbed ethanol with the desorbent selected being capable of direct blending into motor fuel.

7 Claims, 2 Drawing Figures

USE OF ACTIVATED CARBON FOR SEPARATION OF ETHANOL FROM WATER

CROSS REFERENCE TO RELATED APPLICATION

This application is a continuation-in-part of our prior copending application Ser. No. 202,048, filed Oct. 30, 1980, now abandoned incorporated herein by reference.

BACKGROUND OF THE INVENTION

1. Field of the Invention

This field of art to which the claimed invention pertains is solid-bed adsorptive separation. More specifically, the claimed invention relates to a process for the separation of ethanol from a feed mixture comprising ethanol and water which process employs a solid adsorbent which selectively removes the ethanol from the feed mixture.

2. Description of the Prior Art

Diminishing world supplies and availability of crude oil as well as sporadic regional shortfalls of gasoline for motor fuel have created considerable incentive for the development and use of alternative fuels. Ethanol is gaining wide popularity as such a fuel, particularly when mixed with gasoline to form a mixture known as gasohol. Gasohol may contain up to about 10 volume percent ethanol, without modifications to presently used automobile engines being required, thereby extending the volume of motor fuel availability by a like percentage.

The primary source of the ethanol used in gasohol is derived primarily from the fermentation of mash, usually from corn. Natural fermentation is able to produce an ethanol-water product mixture containing at the most about 12 vol.% ethanol. It is therefore necessary to concentrate the ethanol by distillation which, of course, requires a great amount of energy, and, in fact, the greatest cost in production of ethanol by fermentation is the energy required to separate the ethanol from the water by distillation. A means of achieving this separation without such a great expenditure of energy would thus be extremely valuable. One, therefore, might consider the many known adsorptive separation processes known in the art for possible application to the separation of ethanol from water.

For example, it is well-known in the separation art that certain crystalline aluminosilicates can be used to separate hydrocarbon species from mixtures thereof. The separation of normal paraffins from branched chain paraffins, for example, can be accomplished by using a type A zeolite which has pore openings from 3 to about 5 Angstroms. Such a separation process is disclosed in U.S. Pat. Nos. 2,985,589 and 3,201,491. These adsorbents allow a separation based on the physical size differences in the molecules by allowing the smaller or normal hydrocarbons to be passed into the cavities within the zeolitic adsorbent, while excluding the larger or branched chain molecules.

U.S. Pat. Nos. 3,265,750 and 3,510,423, for example, disclose processes in which large pore diameter zeolites such as the type X or type Y structured zeolites can be used to separate olefinic hydrocarbons.

In addition to separating hydrocarbon types, the type X or type Y zeolites have also been employed in processes to separate individual hydrocarbon isomers. In the process described in U.S. Pat. No. 3,114,782, for example, a particular zeolite is used as an adsorbent to separate alkyl-trisubstituted benzene; and in U.S. Pat. No. 3,668,267 a particular zeolite is used to separate specific alkyl-substituted naphthalenes. In processes described in U.S. Pat. Nos. 3,558,732, 3,686,342 and 3,997,620, adsorbents comprising particular zeolites are used to separate para-xylene from feed mixtures comprising para-xylene and at least one other xylene isomer by selectively adsorbing para-xylene over the other xylene isomers. In the last mentioned processes the adsorbents used are para-xylene selective; para-xylene is selectively adsorbed and recovered as an extract component while the rest of the xylenes and ethylbenzenes are all relatively unadsorbed with respect to para-xylene and are recovered as raffinate components. Also, in the last mentioned processes the adsorption and desorption may be continuously carried out in a simulated moving bed countercurrent flow system, the operating principles and sequence of which are described in U.S. Pat. No. 2,985,589.

Unfortunately, with the adsorbents of the above processes separation of ethanol from water would be out of the question because all of those adsorbents are hydrophilic, i.e. they would be selective for water over the ethanol. Thus, in using any of these adsorbents it would be necessary to extract the water which is the major component and reject the ethanol into the raffinate. Also, there would be the problem of what could be used as an effective desorbent. The separation of the desorbent, if possible, from the ethanol raffinate and water extract would be considerably more costly than the primary distillation of the alcohol from the water.

In U.S. Pat. No. 2,474,170 mention is made that activated carbon may be employed as an adsorbent to separate the metabolism products from fermentation processes including the process producing ethyl-alcohol. This reference suggests one of two means for recovering the adsorbed components; (a) treatment of the adsorbent with steam, or (b) heating the adsorbent in vacuo. The first mentioned means would, of course, contaminate the extract stream with water, which would at least partially defeat the purpose for the extraction to begin with, and the latter means would require the costly input of heat and the very costly providing of a vacuum.

We have discovered a hydrophobic adsorbent selective for ethanol over water and a unique means for recovering the ethanol which is particularly suited for the subsequent use of the extract stream in gasohol.

In brief summary, the present invention is, in one embodiment, a process for separating ethanol from a feed mixture comprising ethanol and water. The process comprises contacting, at adsorption conditions, the mixture with an adsorbent comprising activated carbon, selectively adsorbing the ethanol to the substantial exclusion of water, and thereafter recovering high purity ethanol by treating the adsorbent with a desorbent material having utility as a motor fuel ingredient, thereby enabling the extract stream to be used directly for motor fuel blending.

In another embodiment the present invention is a process for separating ethanol from a feed mixture comprising ethanol and water which process comprises contacting at adsorption conditions the mixture with an adsorbent comprising activated carbon which process comprises the steps of: (a) maintaining net fluid flow through a column of the adsorbent in a single direction, which column contains at least three zones having separate operational functions occurring therein and being serially interconnected with the terminal zones of the column connected to provide a continuous connection of the zones; (b) maintaining an adsorption zone in the column, the zone defined by the adsorbent located between a feed inlet stream at an upstream boundary of the zone and a raffinate outlet stream at a downstream boundary of the zone; (c) maintaining a purification zone immediately upstream from the adsorption zone, the purification zone defined by the adsorbent located between an extract outlet stream at an upstream boundary of the purification zone and the feed inlet stream at a downstream boundary of the purification zone; (d) maintaining a desorption zone immediately upstream from the purification zone, the desorption zone defined by the adsorbent located between a desorbent inlet stream at an upstream boundary of the zone and the extract outlet stream at a downstream boundary of the zone; (e) passing the feed stream into the adsorption zone at adsorption conditions to effect the selective adsorption of the ethanol by the adsorbent in the adsorption zone and withdrawing a raffinate outlet stream from the adsorption zone; (f) passing a desorbent material into the desorption zone at desorption conditions to effect the displacement of the ethanol from the adsorbent in the desorption zone, the desorbent material having utility as a motor fuel ingredient; (g) withdrawing an extract stream comprising the ethanol and desorbent material from the desorption zone, the extract stream having the capability of being used directly for motor fuel blending; and (h) periodically advancing through the column of adsorbent in a downstream direction with respect to fluid flow in the adsorption zone, the feed inlet stream, raffinate outlet stream, desorbent inlet stream, and extract outlet stream to effect the shifting of zones through the adsorbent and the production of extract outlet and raffinate outlet streams.

Other objectives and embodiments of the invention encompass details about feed mixtures, adsorbents, desorbent materials and operating conditions, all of which are hereinafter disclosed in the following discussion of each of the facets of the present invention.

DESCRIPTION OF THE INVENTION

Activated carbon as used as an adsorbent in the present invention is the commonly known amorphous form of carbon which is treated to obtain a large surface area (300 to 2000 m$^2$/g). The large surface area implies there exists a highly developed internal pore structure in the activated carbon, thus providing the well-known ability to adsorb gases and vapors and various substances dissolved or dispersed in liquids. Activated carbon used for liquid phase operations, such as decolorizing, is normally a light fluffy powder, while that used for gas phase operations, such as vapor adsorption, is usually a hard, dense granular pellet. The former is commonly derived from bones, wood, peat, lignite and paper mill waste which, to obtain the activated carbon, is reacted with an inorganic chemical compound to degrade or dehydrate the organic molecules during carbonization or calcination, while the latter type of activated carbon is commonly derived from coconut shells, coal, peat and petroleum residues which, to obtain the activated carbon, is first carbonized and then oxidized with air at low temperature, or steam, carbon dioxide, or flue gas at high temperature.

The adsorbents used in the process of this invention can be better understood by brief reference to certain adsorbent properties which are necessary to the successful operation of a selective adsorption process. It will be recognized that improvements in any of these adsorbent characteristics will result in an improved separation process. Among such characteristics are: adsorptive capacity for some volume of an extract component per volume of adsorbent, the selective adsorptive of an extract component with respect to a raffinate component and the desorbent material, sufficiently fast rates of adsorption and desorption of the extract component to and from the adsorbent; and, in instances where the components of the feed mixture are very reactive, little or no catalytic activity for undesired reactions such as polymerization and isomerization.

Feed mixtures to be utilized in the process of this invention will comprise a mixture of ethanol and water. To separate ethanol from a feed mixture containing ethanol and water, the mixture is contacted with the adsorbent and the ethanol is more selectively adsorbed and retained by the adsorbent while the water is relatively unadsorbed and is removed from the interstitial void spaces between the particles of adsorbent and the surface of the adsorbent. The adsorbent containing the ethanol is referred to as a "rich" adsorbent—rich in ethanol.

The more selectively adsorbed feed component is commonly referred to as the extract component of the feed mixture, while the less selectively adsorbed component is referred to as the raffinate component. Fluid streams leaving the adsorbent comprising an extract component and comprising a raffinate component are referred to, respectively, as the extract stream and the raffinate stream. Thus, the raffinate stream will contain as a raffinate component the feed mixture component other than the selected component and the extract stream will contain the selected component a the extract component.

Although it is possible by the process of this invention to produce high purity (98% or greater) ethanol product at high recoveries, it will be appreciated that an extract component is never completely adsorbed by the adsorbent, nor is a raffinate component completely non-adsorbed by the adsorbent. Therefore, small amounts of a raffinate component can appear in the extract stream, and, likewise, small amounts of an extract component can appear in the raffinate stream. The extract and raffinate streams then are further distinguished from each other and from the feed mixture by the ratio of the concentrations of an extract component and a specific raffinate component, both appearing in the particular stream. For example, the ratio of concentration of the more selectively adsorbed ethanol to the concentration of a less selectively adsorbed water will be highest in the extract stream, next highest in the feed mixture, and lowest in the raffinate stream. Likewise, the ratio of the less selectively adsorbed water to the more selectively adsorbed ethanol will be highest in the raffinate stream, next highest in the feed mixture, and the lowest in the extract stream.

The adsorbent can be contained in one or more claims were through programmed flow into and out of the chambers separation of the ethanol is effected. The adsorbent will preferably be contacted with a desorbent material is capable of displacing the adsorbed ethanol from the adsorbent. The resultant extract stream comprising the ethanol and desorbent material may be subjected to a separation step so as to obtain high purity ethanol, however, when the desorbent material is one ordinarily useful for gasoline blending, the ethanol-desorbent mixture could be used directly for that purpose without a need for the separation step. Alternatively, the ethanol could be removed from the adsorbent by purging or by increasing the temperature of the adsorbent or by decreasing the pressure of the chamber or vessel containing the adsorbent or by a combination of these means.

The adsorbent may be employed in the form of a dense compact fixed bed which is alternatively contacted with the feed mixture and desorbent materials. In the simplest embodiment of the invention, the adsorbent is employed in the form of a single static bed in which case the process is only semi-continuous. In another embodiment a set of two or more static beds may be employed in fixed bed contacting with appropriate valving so that the feed mixture is passed through one or more adsorbent beds while the desorbent materials can be passed through one or more of the other beds in the set. The flow of feed mixture and desorbent materials may be either up or down through the desorbent. Any of the conventional apparatus employed in static bed fluid-solid contacting may be used.

Countercurrent moving-bed or simulated moving-bed counter-current flow systems, however, have a much greater separation efficiency than fixed adsorbed bed systems and are therefore preferred for use in our separation process. In the moving-bed or simulated moving-bed processes the adsorption and desorption operations are continuously taking place which allows both continuous production of an extract and a raffinate stream and the continual use of feed and desorbent streams. One preferred embodiment of this process utilizes what is known in the art as the simulated moving-bed countercurrent flow system. The operating principles and sequence of such a flow system are described in U.S. Pat. No. 2,985,589 incorporated herein by reference. In such a system, it is the progressive movement of multiple liquid access points down an adsorbent chamber that simulates the upward movement of adsorbent contained in the chamber. Only four of the access lines are active at any one time; the feed input stream, desorbent inlet stream, raffinate outlet stream, and extract outlet stream access lines. Coincident with this simulated upward movement of the solid adsorbent is the movement of the liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the adsorbent chamber into separate zones, each of which has a different function. In this embodiment of the process, it is generally necessary that three separate operational zones be present in order for the process to take place, although in some instances an optional fourth zone may be used.

The adsorption zone, zone 1, is defined as the adsorbent located between the feed inlet stream and the raffinate outlet stream. In this zone, the feed stock contacts the adsorbent, an extract component is adsorbed, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the adsorbent between the extract outlet stream and the feed inlet stream. The basic operations taking place in zone 2 are the displacement from the non-selective void volume of the adsorbent of any raffinate material carried into zone 2 by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone 3 into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the desorption zone or zone 3. The desorption zone is defined as the adsorbent between the desorbent inlet and the extract outlet stream. The function of the desorption zone is to allow a desorbent material which passes into this zone to displace the extract component which was adsorbed upon the adsorbent during a previous contact with feed in zone 1 in a prior cycle of operation. The flow of fluid in zone 3 is essentially in the same direction as that of zones 1 and 2.

In some instances an optional buffer zone, zone 4, may be utilized. This zone, defined as the adsorbent between the raffinate outlet stream and the desorbent inlet stream, if used, is located immediately upstream with respect to the fluid flow to zone 3. Zone 4 could be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that the raffinate material present in the raffinate stream passing out of zone 1 and into zone 4 can be prevented from passing into zone 3 thereby contaminating extract stream removed from zone 3. In the instances in which the fourth operational zone is not utilized the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically, rotary disc valves which can be utilized in this operation can be found in U.S. Pat. Nos. 3,040,777 and 3,422,848, incorporated herein by reference. Both of the aforementioned patents disclose a rotary type connection valve in which the suitable advancement of the various input and output streams from fixed sources can be achieved without difficulty.

In many instances, one operational zone will contain a much larger quantity of adsorbent than some other operational zone. For instance, in some operations the buffer zone can contain a minor amount of adsorbent as compared to the adsorbent required for the adsorption and purification zones. It can also be seen that in instances in which desorbent is used which can easily desorb extract material from the desorbent that a relatively small amount of adsorbent will be needed in a desorption zone as compared to the adsorbent needed in the buffer zone or adsorption zone or purification zone or all of them. Since it is not required that the adsorbent be located in a single column, the use of multiple chambers or a series of columns is within the scope of the invention.

It is not necessary that all of the input or output streams be simultaneously used, and in fact, in many instances some of the steams can be shut off while others effect an input or output of material. The apparatus which can be utilized to effect the process of this invention can also contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations do not function as a conduit through which material passes into or out of the process.

References can be made to D. B. Broughton U.S. Pat. No. 2,985,589, and to a paper entitled, "Continuous Adsorptive Processing—A New Separation Technique" by D. B. Broughton presented at the 34th Annual Meeting of the Society of Chemical Engineers at Tokyo, Japan, on Apr. 2, 1969, incorporated herein by reference, for further explanation of the simulated moving-bed countercurrent process flow scheme.

Adsorption and desorption conditions for adsorptive separation processes can generally be either in the liquid or vapor phase or both. Preferred adsorption conditions for the process of this invention will include temperatures within the range of from about 20° C. to about 230° C. and will include pressures in the range from about atmospheric to about 500 psig. Pressures higher than about 500 psig do not appear to effect the selectivity to a measurable amount and additionally would increase the cost of the process. Desorption conditions for the process of the invention shall generally include the same range of temperatures and pressures as described for adsorption operations. The desorption of the selectively adsorbed ethanol could also be effected at subatmospheric pressures or elevated temperatures or both or by vacuum purging of the adsorbent to remove the ethanol as suggested in the aforementioned U.S. Pat. No. 2,474,170, but this process is not directed to these desorption methods. The desorbent material relied upon must be judiciously selected to satisfy several criteria. First, the desorbent material must displace the adsorbed ethanol from the adsorbent with reasonable mass flow rates without itself being so strongly adsorbed as to unduly prevent the ethanol from displacing the desorbent material in a following adsorption cycle. Secondly, desorbent materials must be compatible with the particular adsorbent and the particular feed mixture. More specifically, they must not reduce or destroy the critical selectivity of the adsorbent for the ethanol with respect to water. Finally, and in further contradistinction to the prior art, desorbent materials to be used in the process of this invention must additionally be substances which are themselves useful for motor fuel blending. Preferred desorbent material for use in the process of this invention may be one or a mixture of the common ingredients of gasoline, particularly aromatic and other high octane liquid hydrocarbons (at standard conditions) such as isooctane.

A dynamic testing apparatus may be employed to test various adsorbents with a particular feed mixture and desorbent material to measure the adsorbent characteristics of adsorptive capacity, selectivity and exchange rate. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to detect qualitatively or determine quantitatively one or more components in the effluent stream leaving the adsorbent chamber. A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse of feed containing known concentrations of a non-adsorbed tracer and of an ethanol-water mixture, all diluted in desorbent, is injected for a duration of several minutes. Desorbent flow is resumed, and the tracer and the feed components are eluted as in a liquid-solid chromatographic operation. The effluent is collected in fractions and analyzed using chromatographic equipment and traces of the envelopes of corresponding component peaks developed.

From information derived from the test, adsorbent performance can be rated in terms of retention volume for an extract or a raffinate component, selectivity for one component with respect to the other, and the rate of desorption of an extract component by the desorbent. The retention volume of an extract or a raffinate component may be characterized by the distance between the center of the peak envelope of an extract or a raffinate component and the peak envelope of the tracer component or some other known reference point. It is expressed in terms of the volume in cubic centimeters of desorbent pumped during this time interval represented by the distance beween the peak envelopes. Selectivity, (B), for an extract component with respect to a raffinate component may be characterized by the ratio of the distance between the center of the extract component peak envelope and the tracer peak envelope (or other reference point) to the corresponding distance the center of the raffinate component peak envelope and the tracer peak envelope. The rate of exchange of an extract component with the desorbent can generally be characterized by the width of the peak envelopes at half intensity. The narrower the peak width the faster the desorption rate.

Selectivity, (B), with regard to two given components, is equal to the quotient obtained by dividing the respective retention volumes of such components. Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. Ideally, desorbent materials should have a selectivity equal to about 1 or slightly less than 1 with respect to all extract components so that all of the extract components can be desorbed as a class with reasonable flow rates of desorbent material and so that extract components can displace desorbent material in a subsequent adsorption step. While separation of an extract component from a raffinate component is theoretically possible when the selectivity of the adsorbent for the extract component with respect to the raffinate component is greatr than 1.0, it is preferred that such selectivity be greater than 2.0. Like relative volatility, the higher the selectivity the easier the separation is to perform. Higher selectivities permit a smaller amount of adsorbent to be used. The rate of exchange relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

It is also necessary that the adsorbent possess little or no catalytic activity toward any reaction such as polymerization or isomerization of any of the feed components. Such activity might effect adsorbent capacity or selectivity or product yields, or all of these, but in the adsorptive separation of ethanol from water with activated carbon adsorbent, this is generally not a problem.

To further evaluate promising adsorbent systems and to translate this type of data into a practical separation process, actual testing of the best system in a continuous countercurrent liquid-solid contacting device would be ideal. The general operating principles of such a device have been previously described and are found to Broughton U.S. Pat. No. 2,985,589 and a specific laboratory-size apparatus utilizing these principles is described in deRosset et al U.S. Pat. No. 3,706,812. The equipment comprises multiple adsorbent beds with a number of access lines attached to distributors within the beds and terminating at a rotary distributing valve. At a given valve position, feed and desorbent are being introduced through two of the lines and raffinate and extract are withdrawn through two more. All remaining access lines are inactive and when the position of the distributing valve is advaned by one index, all active positions will be advanced by one bed. This simulates a condition in which the adsorbent physically moves in a direction countercurrent to the liquid flow. Additional details on adsorbent testing and evaluation may be found in the paper "Separation of $C_8$ Aromatics by Adsorption" by A. J. deRosset, R. W. Neuzil, A. J. Korous, and D. H. Rosback presented at the American Chemical Society, Los Angeles, Calif., Mar. 28, to Apr. 2, 1971. All of the above references are incorporated herein by reference.

ILLUSTRATIVE EXAMPLES AND DESCRIPTION OF THE DRAWINGS

The following examples are of pulse test results obtained from the above described pulse test apparatus. In all cases the adsorbent column was straight, upflow, with capillary controlled pressure. Feed pulses were 15 ml each and comprised a 50:50 mixture of ethanol and water. The flow was down through the column at a rate of 1.1 ml/min. The adsorbent chamber was packed with adsorbent comprising activated carbon obtained from the Calgon Corporation, a subsidiary of Merck and Company, Inc. The adsorbent comprised hard granules of from 20 to 48 mesh size. The desorbents selected were those capable of direct blending into motor fuel, i.e. high octane hydrocarbons, liquid at standard temperature and conditions.

EXAMPLE 1

In this example, toluene was the desorbent, the temperature was 80° C. and the pressure was sufficient to maintain liquid phase, except two phases existed during the time between effluent volumes of about 10 ml to about 75 ml. The results are shown in FIG. 1 of the drawings. FIG. 1 shows an essentially complete separation of the ethanol and water over a substantial portion of the ethanol elution curve.

EXAMPLE 2

Figure 2:
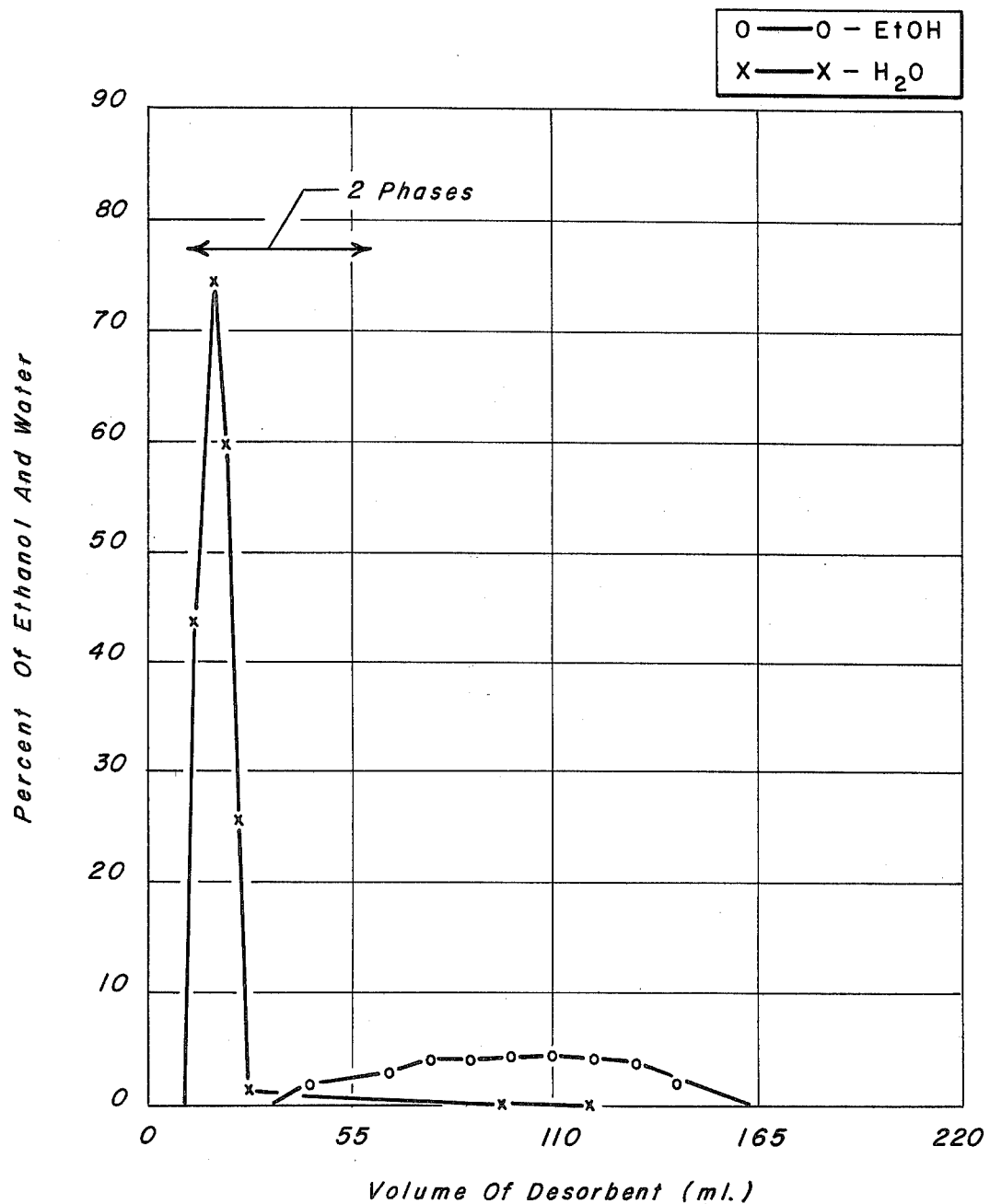

In this example, the desorbent was a 15:85 toluene:isooctane blend, which may be considered a gasoline, and, of course, which would be ideal for motor fuel blending. The temperature was 80° C. and the pressure was sufficient to maintain liquid phase, except two phases existed during the time between effluent volumes of about 10 ml to about 60 ml. The results are shown in FIG. 2 of the drawings. FIG. 2 also shows an essentially complete separation of the ethanol and water over a substantial portion of the last part of the ethanol elution curve as well as a very minor amount of water contamination or "tailing" over almost all of the preceding part of that curve. The present invention is thus capable of yielding gasohol directly as an extract stream and containing essentially anhydrous ethanol.

We claim as our invention:

1. A process for separating ethanol from a feed mixture comprising ethanol and water and for producing a motor fuel blend, which process comprises contacting said mixture at adsorption conditions with an adsorbent comprising activated carbon, selectively adsorbing said ethanol in said adsorbent to the substantial exclusion of water, contacting the adsorbent containing the adsorbed ethanol with a desorbent material comprising a high octane hydrocarbon boiling in the gasoline range to desorb said ethanol from the adsorbent, and removing from said adsorbent and recovering as said motor fuel blend the resultant mixture of ethanol and desorbent material.

2. The process of claim 1 further characterized in that said desorbent material comprises isooctane.

3. The process of claim 1 further characterized in that said adsorption conditions include a temperature within the range of from about 20° C. to about 230° C. and at a pressure within the range of from about atmospheric to about 500 psig.

4. The process of claim 1 which further comprises the steps of:
  (a) maintaining net fluid flow through a column of said adsorbent in a single direction, which column contains at least three zones having separate operational functions occurring therein and being serially interconnected with the terminal zones of said column connected to provide a continuous connection of said zones;
  (b) maintaining an adsorption zone in said column, said zone defined by the adsorbent located between a feed inlet stream at an upstream boundary of said zone and a raffinate oulet stream at a downstream boundary of said zone;
  (c) maintaining a purification zone immediately upstream from said adsorption zone, said purification zone defined by the adsorbent located between an extract outlet stream at an upstream boundary of said purification zone and said feed inlet stream at a downstream boundary of said purification zone;
  (d) maintaining a desorption zone immediately upstream from said purification zone, said desorption zone defined by the adsorbent located between a desorbent inlet stream at an upstream boundary of said zone and said extract outlet stream at a downstream boundary of said zone;
  (e) passing said feed stream into said adsorption zone at adsorption conditions to effect the selective adsorption of said ethanol by said adsorption in said adsorption zone and withdrawing a raffinate outlet stream from said adsorption zone;
  (f) passing a desorbent material into said desorption zone at desorption conditions to effect the displacement of said ethanol from the adsorbent in said desorption zone, said desorbent material having utility as a motor fuel ingredient;
  (g) withdrawing an extract stream comprising said ethanol and desorbent material from said desorption zone, said extent stream having the capability of being used directly for motor fuel blending;
  (h) periodically advancing through said column of adsorbent in a downstream direction with respect to fluid flow in said adsorption zone the feed inlet stream, raffinate outlet stream, desorbent inlet stream, and extract outlet stream to effect the shifting of zones through said adsorbent and the production of extract outlet and raffinate outlet streams.

5. The process as described in claim 4 further characterized in that said desorbent material comprises isooctane.

6. The process of claim 4 further characterized in that it includes the step of maintaining a buffer zone immediately upstream from said desorption zone, said buffer zone defined as the adsorbent located between the desorbent input stream at a downstream boundary of said buffer zone and a raffinate output stream at an upstream boundary of said buffer zone.

7. The process of claim 4 further characterized in that said adsorption conditions and desorption conditions include a temperature within the range of from about 20° C. to about 230° C. and a pressure within the range of from about atmospheric to about 500 psig.

* * * * *